US010172530B2

(12) United States Patent
Takahashi

(10) Patent No.: US 10,172,530 B2
(45) Date of Patent: Jan. 8, 2019

(54) BIOLOGICAL INFORMATION PROCESSING SYSTEM AND METHOD OF CONTROLLING BIOLOGICAL INFORMATION PROCESSING SYSTEM

(71) Applicant: Seiko Epson Corporation, Tokyo (JP)

(72) Inventor: Eizo Takahashi, Asahi-mura (JP)

(73) Assignee: Seiko Epson Corporation, Tokyo (JP)

( * ) Notice: Subject to any disclaimer, the term of this patent is extended or adjusted under 35 U.S.C. 154(b) by 301 days.

(21) Appl. No.: 14/791,002

(22) Filed: Jul. 2, 2015

(65) Prior Publication Data
US 2016/0007868 A1 Jan. 14, 2016

(30) Foreign Application Priority Data

Jul. 9, 2014 (JP) ................................ 2014-141124

(51) Int. Cl.
*A61B 5/024* (2006.01)
*A61B 5/00* (2006.01)

(52) U.S. Cl.
CPC ........ *A61B 5/02438* (2013.01); *A61B 5/4058* (2013.01); *A61B 5/4812* (2013.01); *A61B 5/681* (2013.01); *A61B 5/4064* (2013.01); *A61B 5/4815* (2013.01); *A61B 5/7275* (2013.01)

(58) Field of Classification Search
CPC .. A61B 5/02438; A61B 5/4812; A61B 5/4815
See application file for complete search history.

(56) References Cited

U.S. PATENT DOCUMENTS

| 2005/0043652 | A1* | 2/2005 | Lovett ...................... A61B 5/00 600/595 |
| 2012/0323085 | A1 | 12/2012 | Takeda |
| 2014/0088378 | A1 | 3/2014 | Muzet |
| 2016/0007931 | A1* | 1/2016 | Rubin ................ A61B 5/02438 600/484 |

FOREIGN PATENT DOCUMENTS

| JP | 2001-061819 A | 3/2001 |
| JP | 2013-052165 A | 3/2013 |

OTHER PUBLICATIONS

Gennaro, et al., "EEG Arousals in Normal Sleep: Variations Induced by Total and Selective Slow-wave Sleep Deprivation," SLEEP, vol. 24. No. 6, pp. 673-679 (2001).

* cited by examiner

*Primary Examiner* — William Levicky
(74) *Attorney, Agent, or Firm* — Kilpatrick Townsend & Stockton LLP

(57) ABSTRACT

A biological information processing system includes a pulse wave information acquisition unit which acquires pulse wave information of a user, and a processing unit which determines the sleep state of the user based on the pulse wave information. The processing unit obtains index information relating to an arousal state during sleep based on the pulse wave information.

11 Claims, 13 Drawing Sheets

PULSE AC

| AGE | Pk | RESPONSIVENESS |
|---|---|---|
| 20 TO LESS THAN 30 | $3\sigma$ | HIGH |
| 30 TO LESS THAN 40 | $3\sigma$ | HIGH |
| 40 TO LESS THAN 50 | $2.58\sigma$ | STANDARD |
| 50 TO LESS THAN 60 | $1.96\sigma$ | LOW |
| 60 TO | $1.96\sigma$ | LOW |

BIOLOGICAL INFORMATION PROCESSING SYSTEM AND METHOD OF CONTROLLING BIOLOGICAL INFORMATION PROCESSING SYSTEM

This application claims priority to Japanese Patent Application No. 2014-141124, filed Jul. 9, 2014, the entirety of which is hereby incorporated by reference.

BACKGROUND

1. Technical Field

The present invention relates to a biological information processing system, a method of controlling a biological information processing system, and the like.

2. Related Art

In recent years, studies of a sleep state have been advanced. For example, the depth of sleep or the like can be determined using brain waves. Specifically, a PSG measurement method (R&K method) is known. In the R&K method, a plurality of electrodes are mounted on a face or a head of a user, and a sleep state is determined based on brain waves, eye movement, electromyography, and the like.

It is well known that the state of sleep affects the physical condition or the like of the user in an awake state. A method which presents information relating to a sleep state, which the user cannot recognize, to the user in a certain form is disclosed. For example, JP-A-2001-61819 discloses a method which acquires information relating to the sleep state of a user, presents information relating to the quality of sleep, and provides advice to the user.

In the determination of the sleep state using brain waves and the like, the sleep state is classified into a REM sleep state and a non-REM sleep state, and the non-REM sleep state is divided into Stage 1 to Stage 4 according to the depth of sleep. From a viewpoint different from the depth of sleep, a reaction, called arousal, which is transient awake in the brain waves, is also detected. For example, Gennaro et al. EEG Arousal in Normal Sleep: Variations Induced by Total and Selective Slow-wave Sleep Deprivation. SLEEP, Vol. 24, No. 6, 2001 discloses arousal.

In JP-A-2001-61819, while the quality of sleep is evaluated and advice is provided, there is no disclosure of a specific determination method of a sleep state, and in particular, arousal described in Gennaro et al. EEG Arousal in Normal Sleep: Variations Induced by Total and Selective Slow-wave Sleep Deprivation. SLEEP, Vol. 24, No. 6, 2001 is not considered.

As described above, a sensor (for example, a plurality of electrodes) which detects brain waves is used, whereby it is possible to determine a sleep state with excellent accuracy and to detect arousal. However, the brain waves need to be measured in a specialized institution, such as a medical institution. While a method (device) which comparatively easily perform a brain wave measurement by decreasing the number of electrodes to be used is suggested, it is not easy to use this method in an ordinary household on a daily basis.

SUMMARY

An advantage of some aspects of the invention is to provide a biological information processing system, a method of controlling a biological information processing system, and the like capable of easily detecting an arousal state using pulse wave information and obtaining index information based on the detection result.

An aspect of the invention relates to a biological information processing system including a pulse wave information acquisition unit which acquires pulse wave information of a user, and a processing unit which determines the sleep state of the user based on the pulse wave information. The processing unit obtains index information relating to an arousal state during sleep based on the pulse wave information.

In the aspect of the invention, the index information relating to the arousal state during sleep is obtained based on the pulse wave information. With this, it is possible to easily obtain the index information relating to the arousal state compared to a method using brain waves and the like. Since the obtained index information is information relating to the arousal state, it is possible to perform more detailed determination relating to the sleep state compared to the determination that the sleep state is an awake state.

In the aspect of the invention, the processing unit may obtain the index information based on a change in the pulse wave information in a first period during which it is determined that the user is in the sleep state.

With this configuration, it is possible to perform an efficient process by targeting the pulse wave information in a period during which it is determined to be the sleep state.

In the aspect of the invention, the processing unit may obtain the index information based on a comparison process of the amount of change in the pulse wave information in a given second period and a pulse wave change amount threshold value.

With this configuration, it is possible to obtain the index information by the threshold value determination using the amount of change in the pulse wave information within a predetermined time interval.

In the aspect of the invention, the processing unit may obtain, as index information, the number of times at which the amount of change in the pulse wave information in the second period exceeds the pulse wave change amount threshold value for a given unit time. The pulse wave change amount threshold value is, for example, a threshold value relating to an amount of change in a pulse rate.

With this configuration, it is possible to use the number of times, at which the threshold value per given unit time is exceeded, as the index information.

In the aspect of the invention, the processing unit may set at least one value of the given time interval and the pulse wave change amount threshold value based on personal information of the user.

With this configuration, it is possible to flexibly set at least one of the given time interval and the pulse wave change amount threshold value for use when obtaining the index information based on information of the user.

In the aspect of the invention, the pulse wave information may be information representing a pulse rate or a pulse period, and the processing unit may set the length of the second period based on a time corresponding to a change cycle of the pulse wave information.

With this configuration, it is possible to set the length of the second period based on the pulse rate, the pulse period, or the change cycle of information representing the pulse rate or the pulse period.

In the aspect of the invention, the processing unit may perform a smoothing process of the pulse wave information in a first period during which it is determined that the user is in the sleep state, may obtain a change of the pulse wave information before the smoothing process with respect to the value of the pulse wave information after the smoothing process as the amount of change in the pulse wave information, when the amount of change exceeds a pulse wave change amount threshold value, may obtain a time representing the width of a peak of the pulse wave information corresponding to the amount of change, and when the obtained time is within a given second period, may determine that the arousal state is generated and may obtain the index information based on the determination result.

With this configuration, it is possible to obtain the index information relating to the arousal state by performing a process according to a specific procedure.

In the aspect of the invention, the processing unit may obtain somnolence index information as the index information relating to the arousal state.

With this configuration, it is possible to obtain the somnolence index information as the index information relating to the arousal state.

In the aspect of the invention, the processing unit may detect a state representing awakening without user consciousness as the arousal state based on the pulse wave information.

With this configuration, it is possible to detect a state representing transient awakening without user consciousness as the arousal state.

In the aspect of the invention, the pulse wave information may be a pulse rate or a pulse period.

With this configuration, it is possible to use the pulse rate or the pulse period as the pulse wave information.

In the aspect of the invention, the biological information processing system may further a presentation unit which presents the index information to the user.

With this configuration, it is possible to present the obtained index information in the biological information processing system.

In the aspect of the invention, the presentation unit may present that the user is in the arousal state.

With this configuration, it is possible to directly present that the user is in the arousal state.

Another aspect of the invention relates to a biological information processing system in which pulse wave information of a user is acquired, and information relating to an arousal state during sleep is obtained based on the pulse wave information.

In the aspect of the invention, information relating to the arousal state during sleep is obtained based on the pulse wave information. With this, it is possible to easily obtain information relating to the arousal state compared to a method using brain waves and the like. For this reason, the obtained information is used, whereby it is possible to perform more detailed determination relating to the sleep state compared to the determination that the sleep state is an awake state.

In the aspect of the invention, the sleep state of the user may be determined based on the pulse wave information.

With this configuration, it is possible to perform sleep state determination based on the pulse wave information.

In the aspect of the invention, information relating to the arousal state may be presented.

With this configuration, it is possible to present the obtained information in the biological information processing system.

In the aspect of the invention, information relating to the arousal state may be the number of times at which the amount of change in the pulse wave information in a given second period exceeds a pulse wave change amount threshold value for a given unit time.

With this configuration, it is possible to use the number of times, at which the threshold value per given unit time is exceeded, as information relating to the arousal state.

In the aspect of the invention, sleepiness prediction indicating a possibility of the user feeling sleepy may be presented based on information relating to the arousal state.

With this configuration, it becomes possible to present information representing the arousal state to the user who is likely to feel sleepy, in an easy-to-understand form.

Still another aspect of the invention relates to a method of controlling a biological information processing system including performing a process for acquiring pulse wave information of a user, and performing a process for obtaining information relating to an arousal state during sleep based on the pulse wave information.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, this embodiment will be described. This embodiment described below is not intended to unduly limit the content of the invention described in the appended claims. It is not always true that all elements described in this embodiment are essential constituent elements of the invention.

1. Method of this Embodiment

First, a method of this embodiment will be described. It is well known that a sleep state affects the health of a user. For example, it is already general knowledge that lack of sleep leads to various symptoms, such as sleepiness, fatigue, nausea, and dizziness.

Furthermore, it is found that, instead of a simple sleep time, the state of sleep affects the health of the user. For example, a method is known in which sleep includes a REM sleep state and a non-REM sleep state, and the non-REM sleep state is divided into four stages according to the depth of sleep. In this division, Stage 3 or 4 of the non-REM sleep state is a very deep sleep state. For a user who does not undergo the state of deep sleep during sleep, the quality of sleep is bad, and even if a sufficient sleep time is secured, a symptom, such as sleepiness or fatigue, occurs.

While the user may recognize any symptom for the sleep time, in order to acquire detailed information of the sleep state, a process using a certain sensor is required. As the determination of the sleep state, a PSG measurement method (R&K method) which measures brain waves and the like is well known. Specifically, a plurality (for example, tens) of electrodes for brain wave detection are mounted on the head of the user, and a sleep state is determined using brain waves having different characteristics being detected according to the state (depth) of sleep.

As disclosed in Gennaro et al. EEG Arousal in Normal Sleep: Variations Induced by Total and Selective Slow-wave Sleep Deprivation. SLEEP, Vol. 24, No. 6, 2001, arousal which is transient awakening in brain waves may be detected using brain waves and the like. As the factors for arousal, various factors including a respiration disorder, a cyclic limb movement disorder, certain pains, psychological factors, such as stress, and the like are considered. In all cases, when the number of instances of arousal is greater than a normal range, it can be estimated that the quality of sleep is bad.

In a case where brain waves are used, it is possible to determine the sleep state with excellent accuracy. However, the brain waves need to be measured in a specialized institution, such as a medical institution. A method (device) in which a brain wave measurement is comparatively easily performed by decreasing the number of electrodes to be used is decreased or constituting a plurality of electrodes integrally in a single device has been suggested; however, it is not easy to use this method in an ordinary household on a daily basis.

Figure 1:
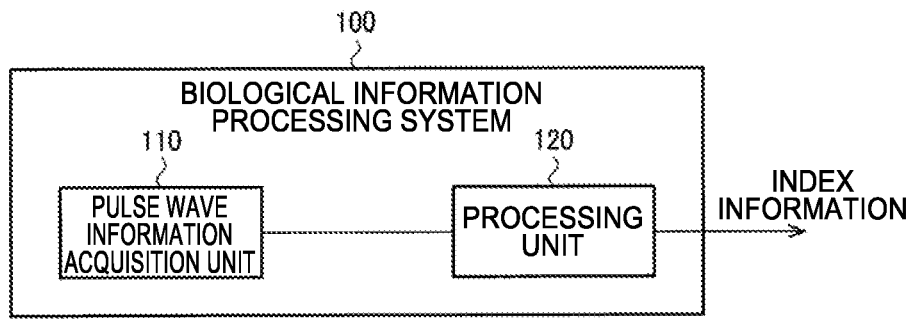
FIG. 1 shows a configuration example of a biological information processing system according to this embodiment.

Accordingly, the applicants suggest a method which acquires pulse wave information of a user with a pulse wave sensor, and performs a process relating to arousal using the pulse wave information. Specifically, as shown in FIG. 1, a biological information processing system 100 according to this embodiment includes a pulse wave information acquisition unit 110 which acquires pulse wave information of a user, and a processing unit 120 which determines the sleep state of the user based on the pulse wave information. The processing unit 120 obtains index information relating to an arousal state during sleep based on the pulse wave information.

As described above, the arousal state is transient awakening in the brain waves, and represents a state different from an awake state (Stage Wake) in the R&K method or the like. In general, the arousal state is awakening (unconscious awakening) without user consciousness. Specifically, the awake state represents a state where the instance of α waves per unit time (1 epoch, for example, 30 seconds) becomes equal to or greater than 50%, and the arousal state represents a state where a change in a brain wave frequency of three seconds or more occurs. The details of the sleep state, the awake state, and the arousal state will be described below.

That is, specifically, the processing unit 120 may detect a state representing awakening (specifically, transient awakening) without user consciousness as the arousal state based on pulse wave information. Then, it is possible to detect the arousal state and to obtain index information based on the detection result. Even a healthy user undergoes the arousal state about 20 times per hour; however, when a user undergoes the arousal state an excessively large number of times, the quality of sleep is bad (for example, the time of deep sleep, such as Stage 3 or 4, is extremely short) and may affect health or the like. However, even if the arousal state is detected, when the duration thereof is less than 15 seconds, the detection period of α waves in a unit time is less than 50%, and it is determined to be the sleep state. That is, although the arousal state is information representing the quality of sleep, information relating to the arousal state falls in obscurity by determining only the sleep state and the awake state. From this point, according to the method of this embodiment, it is possible to detect the arousal state and to obtain index information, whereby it is possible to present the index information to the user, a family, a doctor in charge, or the like.

Figure 6:
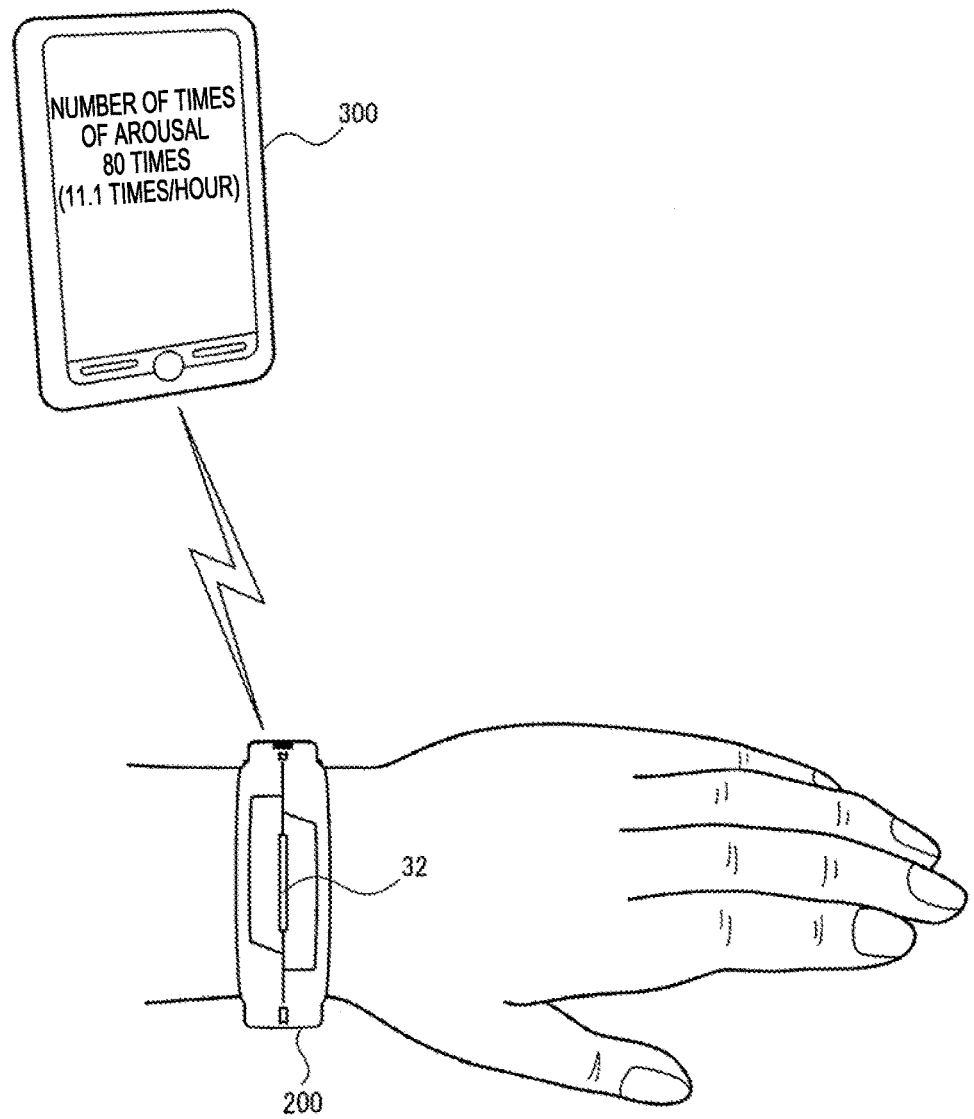
FIG. 6 shows a mounting example of the biological information processing system (wearable apparatus) and a display example of index information in a mobile terminal apparatus.

In this embodiment, it is possible to implement a process for obtaining the index information using the pulse wave information. A pulse wave sensor for acquiring the pulse wave information can be implemented by, for example, a photoelectric sensor, and the photoelectric sensor may be constituted by combining a light emitting part (for example, LED) and a light receiving part (for example, PD) and can be thus easily implemented by hardware. Even if a plurality of sets of LEDs and PDs are provided in consideration of improvement of accuracy or the like, it is possible to reduce the size of the sensor unit or the entire device. There is less need to mount the sensor in a plurality of different places like brain waves, and there is no problem, for example, even if the mounting place is only a wrist as shown in FIG. 6. That is, a device for pulse wave detection is easily able to be reduced in cost or size and weight, and difficulty when mounting the device should not be a problem. Therefore, it is advantageous compared to brain wave detection.

Information obtained by the biological information processing system 100 of this embodiment is not limited to the index information. Specifically, the biological information processing system 100 may acquire pulse wave information of the user and may obtain information relating to an arousal state during sleep based on the pulse wave information.

The index information relating to the arousal state is information indicating the degree of the sleep state obtained based on the arousal state. For this reason, as described below referring to FIGS. 15A to 15C, specifically, the index information becomes information representing the degree of sleepiness the next day, the degree of the depth of sleep, or the number of instances of the arousal state representing the degree of sleepiness or the degree of the depth of sleep.

In contrast, information relating to the arousal state may be the above-described index information, or may be a different kind of information. For example, when the user is in the arousal state, information representing the effect may be information relating to the arousal state. Since the user is obviously in the sleep state, the user cannot read information in real time; however, a family member who lives with the user can confirm information, or if the user is in the hospital, a doctor in charge can confirm information.

In this case, the biological information processing system 100 may have a presentation unit (for example, a display unit 160 or the like described below referring to FIG. 3). The presentation unit presents that the user is in an arousal state. Then, it is possible to directly confirm that the user is in the arousal state, and for example, to examine user behavior or the like before and after the timing of becoming the arousal state.

Information indicating that the arousal state is detected around at specific hour, specific minute, and specific second may be stored, and information also becomes information relating to the arousal state. Then, it is possible to manage detailed information of the timing of becoming the arousal state or the like. For example, it is also possible to examine the trend of each user that the frequency at which a target user is in an arousal state in the second half of the sleep state is increased. Furthermore, if video of the user during sleep is imaged, it is possible to efficiently examine user behavior or the like in the arousal state by combining the above-described detailed information and video.

Hereinafter, first, the sleep state, the awake state, and the arousal state will be described in detail. Thereafter, the configuration of the biological information processing system 100 according to this embodiment will be described, and the details of an arousal detection method based on pulse wave information will be described. Next, an example of a display screen when presenting the obtained index information relating to the arousal state to the user or the like will be described, and finally, a method of determining the sleep state or the like based on the pulse wave information will be described.

2. Sleep State, Awake State (Wake), Arousal

The awake state (Stage Wake) in this embodiment refers to a state where α waves are detected in 50% or more of a predetermined period. In contrast, α waves gradually diminish in a transition period from the awake state to the sleep state (in particular, Stage 1), and a state where α waves are less than 50% of the predetermined period is Stage 1 of the non-REM sleep state.

In a transition period from Stage 1 to Stage 2, slow waves having high amplitude gradually appear. A state where spindle (spindle wave) or K-complex appears is Stage 2. Spindle is a waveform of 12 to 14 Hz having a duration of 0.5 seconds or more, and K-complex is a negative-positive wave having a duration of 0.5 seconds or more.

A state where slow waves (δ waves) of 2 Hz or less and 75 μV or more occupy 20 to 50% of a predetermined period is Stage 3, and a state where δ waves become 50% or more is Stage 4. Strictly, in the determination of each Stage, eye movement or jaw muscle activity is used but is omitted for simplification of description.

The REM sleep state is a state where the state of brain waves is the same as Stage 1 of the non-REM sleep state and rapid eye movements (REMs) are found. Furthermore, jaw muscle activity is most inactive during the night in the REM sleep state. In addition, in the determination of the REM sleep state, determination regarding whether or not sawtooth waves appear in brain waves is performed.

Figure 2:
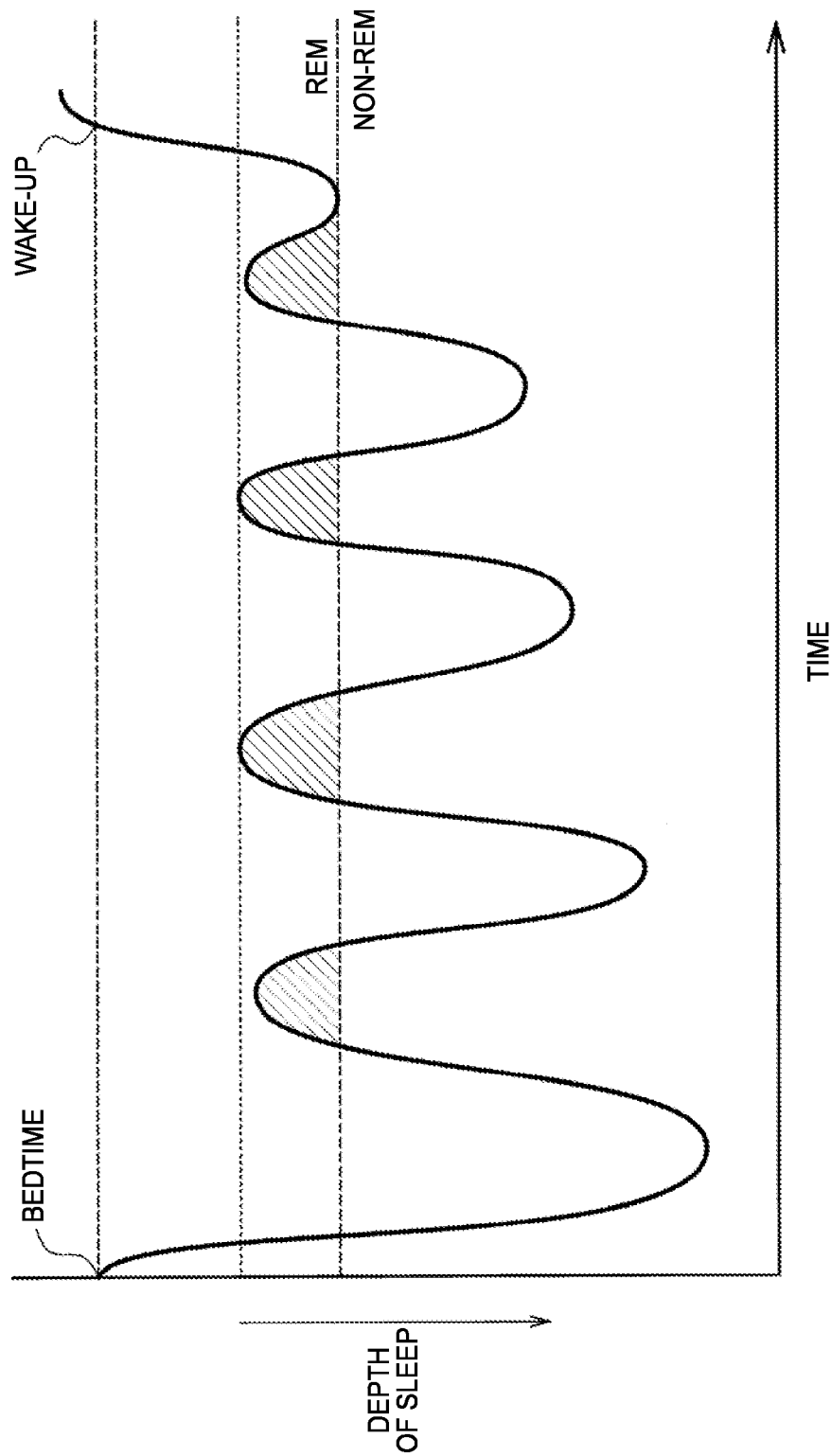
FIG. 2 shows an example of a temporal change in the depth of sleep in a sleep state.

As shown in FIG. 2, it is known that, from the time when a person falls asleep until the person wakes up, the depth of sleep changes cyclically with time. Specifically, the non-REM sleep state and the REM sleep state alternately appear in a cycle of about one hour and half. Deep sleep, such as Stage 3 or Stage 4, appears in the first half of sleep, and light sleep, such as Stage 1 or Stage 2 of non-REM sleep, appears in the second half of sleep (the time close to wake-up).

In contrast, arousal is transient awakening in brain waves, and in general, at the time of arousal, the user does not wake up. The instance frequency of arousal varies depending on age; however, the instance frequency of arousal of a healthy user is 10 to 20 times per hour. When brain waves are used, arousal is detected as a shift in a brain wave frequency. Specifically, when there is a preceding apparent sleep state which is persistent for ten seconds or more and a shift in a brain wave frequency having a duration of three seconds or more is detected, it is assumed that a single arousal state is detected. Conversely, even if a shift in a brain wave frequency is detected, when the preceding sleep state is less than ten seconds, or the duration of the shift in the brain wave frequency is less than three seconds, it is not determined to be the arousal state. In regard to arousal, strictly, other determination conditions, such as jaw muscle activity, are used, but detailed description thereof will be omitted.

Since arousal disrupts sleep, when the detection frequency of arousal exceeds a normal range (for example, the number of times per hour is greater than 20), similarly to short sleep, the quality of sleep is bad and a problem, such as sleepiness of the user, may occur. That is, the number of times (frequency) of arousal can be used as index information relating to the sleep state of the user.

The above description is the definition of each state when brain waves or the like are used. In this embodiment, the definition of each state follows the above description; however, as described above, in this embodiment, pulse wave information, instead of brain waves, is used for a process. Because the pulse wave information is used, α waves, δ waves, and the like cannot be directly observed. Therefore, it is not possible to perform state determination according to whether or not the above-described definition is satisfied. As described below, the arousal state is determined using the amount of change in a pulse rate (heart rate), instead of a shift in a brain wave frequency.

That is, each state in this embodiment is estimated as the state by determination based on pulse wave information, and if determination accuracy is considered, the possibility that the determination result does not satisfy the above-described definition cannot be denied. However, in regard to a method of determining a sleep state using a pulse wave state, various methods including a method using HF and LF are known, and it is found that the same result as when brain waves are used with sufficiently high accuracy (for example, equal to or higher than 70 to 80%) is obtained.

3. System Configuration Example

As shown in FIG. 1, the biological information processing system 100 according to this embodiment includes a pulse wave information acquisition unit 110 and a processing unit 120. The pulse wave information acquisition unit 110 acquires sensor information from a pulse wave sensor. The pulse wave sensor is a sensor for detecting a pulse wave signal, and for example, a photoelectric sensor including a light emitting part and a light receiving part, or the like is considered. It is known that the pulse wave sensor can be implemented by various sensors, such as a photoelectric sensor or other types of sensors (for example, an ultrasonic sensor), and the pulse wave sensor of this embodiment can widely apply these sensors.

The processing unit 120 performs determination relating to the sleep state based on the pulse wave information acquired by the pulse wave information acquisition unit 110 and obtains index information regarding the arousal state. The processing unit 120 may perform the determination process regarding the arousal state in a narrow sense; however, the invention is not limited thereto, and other processes may be performed. For example, as described below referring to FIGS. 9A, 9B, and the like, determination of the REM sleep state or non-REM sleep state may be performed, or when the sleep state is the non-REM sleep state, determination of any stage of Stages 1 to 4 may be performed. The function of the processing unit 120 can be implemented by hardware, such as various processors (CPU or the like) or ASIC (a gate array or the like), a program, or the like.

However, the biological information processing system 100 is not limited to the configuration of FIG. 1, and various modifications can be made by omitting some constituent elements or adding other constituent elements. Similarly, in FIG. 3, modifications can be made.

The biological information processing system 100 of this embodiment may be implemented by various electronic apparatuses. An electronic apparatus may be a biological information measurement apparatus, or may be a wearable apparatus which is mounted on the user in a narrow sense. In this case, index information relating to the arousal state is obtained in a wearable apparatus which is an electronic apparatus according to this embodiment.

Figure 3:
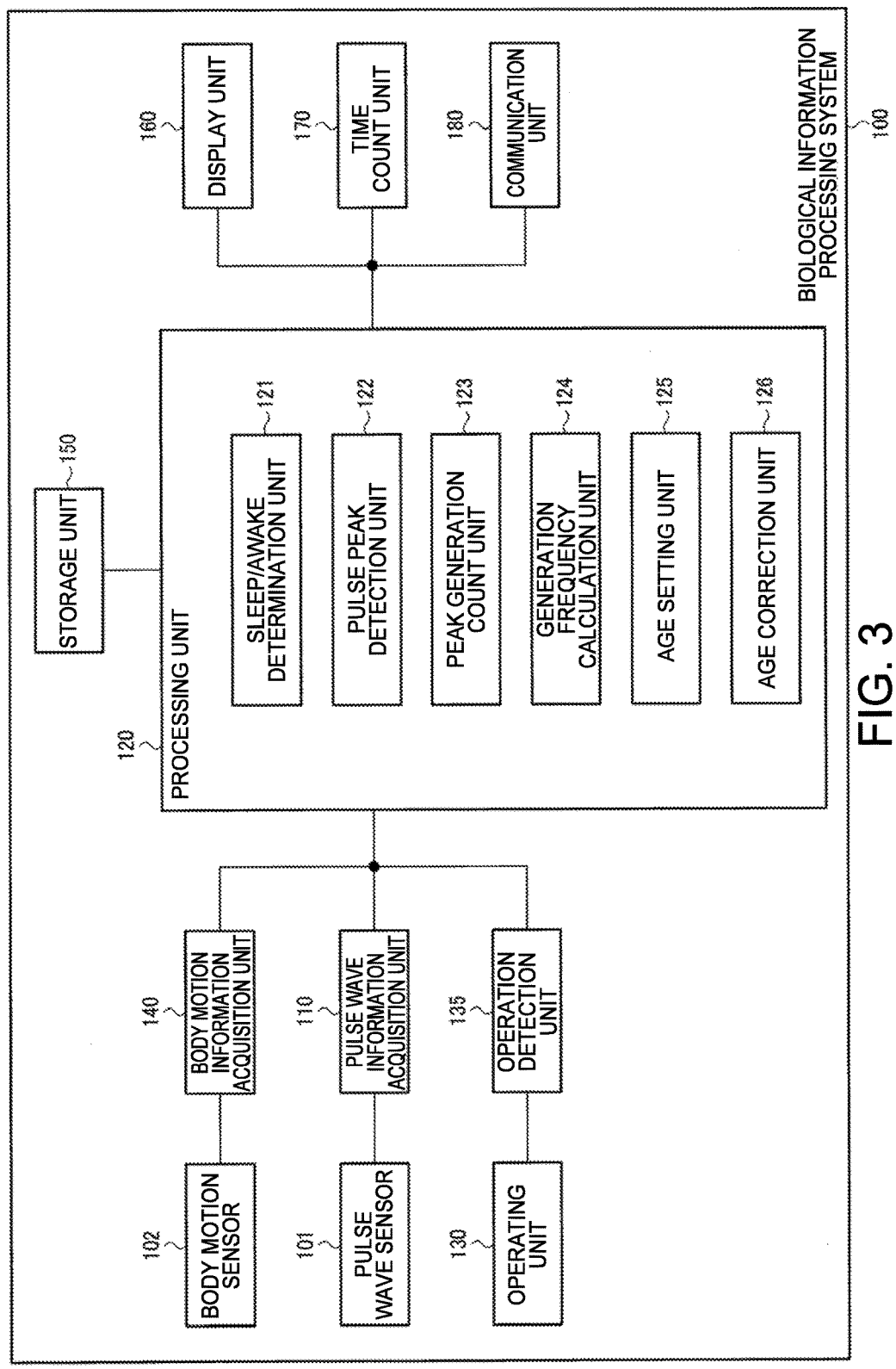
FIG. 3 shows a detailed configuration example of the biological information processing system according to this embodiment.

Specifically, as shown in FIG. 3, the electronic apparatus (wearable apparatus 200) according to this embodiment may include a pulse wave sensor 101, a body motion sensor 102, a pulse wave information acquisition unit 110, a processing unit 120, an operating unit 130, an operation detection unit 135, a body motion information acquisition unit 140, a storage unit 150, a display unit 160, a time count unit 170, and a communication unit 180.

The processing unit 120 includes a sleep/awake determination unit 121, a pulse peak detection unit 122, a peak generation count unit 123, a generation frequency calculation unit 124, an age setting unit 125, and an age correction unit 126.

The body motion sensor 102 is a sensor which detects the body motion of the user, and various sensors, such as an acceleration sensor and a gyro sensor, can be used. The body motion information acquisition unit 140 acquires body motion information representing the body motion of the user based on sensor information from the body motion sensor 102.

The sleep/awake determination unit 121 of the processing unit 120 determines whether the user is in the sleep state or the awake state. The sleep/awake determination unit 121 may perform determination of a stage (depth) in the sleep state. Specifically, a method described below may be executed using FIGS. 9A, 9B, and the like.

The pulse peak detection unit 122 detects a peak of a pulse rate. Specifically, a process for obtaining $\Delta P$ described below is performed. In the pulse peak detection unit 122, a value when $\Delta P > Pk$ and a time $\Delta t$ corresponding to a peak width becomes $\Delta t \leq tw$ is detected as a peak. The details of $\Delta P$, $Pk$, $\Delta t$, and $tw$ will be described below. The peak generation count unit 123 counts the number of times of generation (the number of times of detection) of a peak.

The generation frequency calculation unit 124 obtains the number of peaks per unit time (for example, one hour) from the number of peaks counted by the peak generation count unit 123. The age setting unit 125 sets the age of the user. For example, the age of the user may be set based on information input from the user using the operating unit 130. The age correction unit 126 performs a correction process of various parameters based on the age of the user set by the age setting unit 125. A parameter to be corrected is, for example, the value of a pulse wave change amount threshold value $Pk$.

The operating unit 130 receives operation by the user. Specifically, the operating unit 130 may be implemented by a physical button or a lever, or may be implemented using a touch panel or the like. Furthermore, vibration caused by the user tapping the apparatus may be used as an interface, and in this case, the body motion sensor 102 may be used as the operating unit 130. The operation detection unit 135 detects operation by the user based on a signal from the operating unit 130.

The storage unit 150 becomes a work area of the processing unit 120 or the like, and the function thereof can be implemented by a memory, such as a RAM, a hard disk drive (HDD), or the like. The storage unit 150 may store the pulse wave information, the determination result of the sleep state, and the like.

The display unit 160 displays various display screens, and for example, may present the index information regarding the arousal state. The display unit 160 can be implemented by a liquid crystal display, an organic EL display, or the like. In the biological information processing system 100, the display unit 160 may be omitted, and in this case, the presentation of information to the user may be performed by other methods. For example, the biological information processing system 100 may have a light emitting part and may present information through light emission of the light emitting part, or may have a vibration part and may present information through vibration of the vibration part.

The time count unit 170 measures a time. The communication unit 180 performs communication with other apparatuses through various networks or the like. As described below referring to FIGS. 6 and 7, it is also considered to notify the obtained index information to other apparatuses. Therefore, in this case, the obtained index information or information (for example, information of a display screen or the like) for presenting the index information is transmitted to other apparatuses.

Figure 4A:
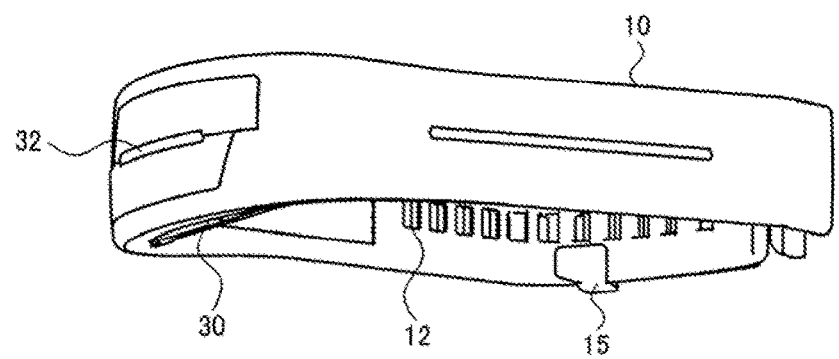
FIGS. 4A and 4B are appearance diagrams of the biological information processing system (wearable apparatus) of this embodiment.
Figure 4B:
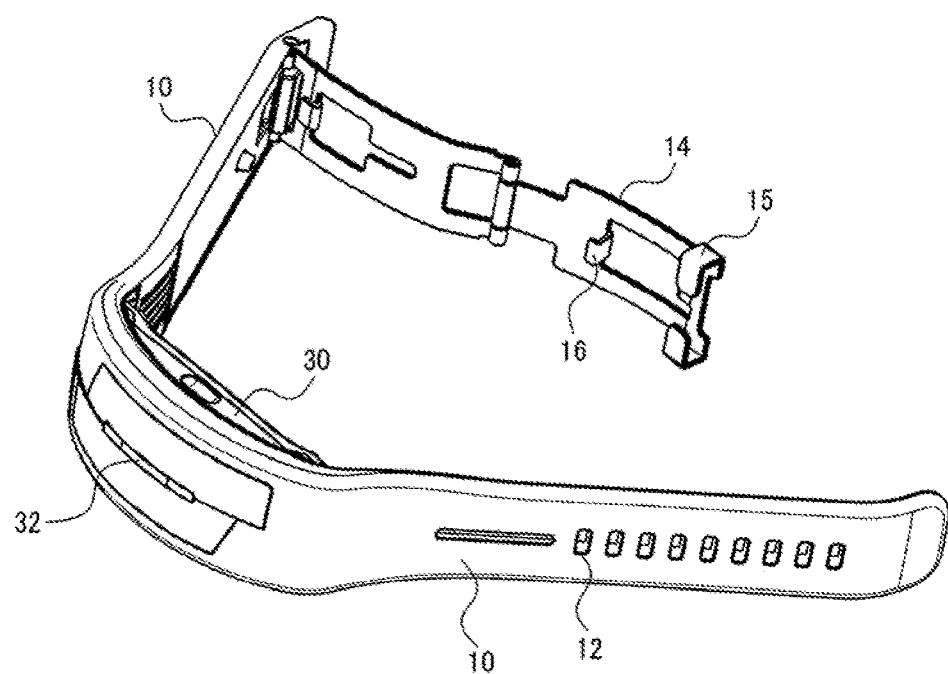
Figure 5:
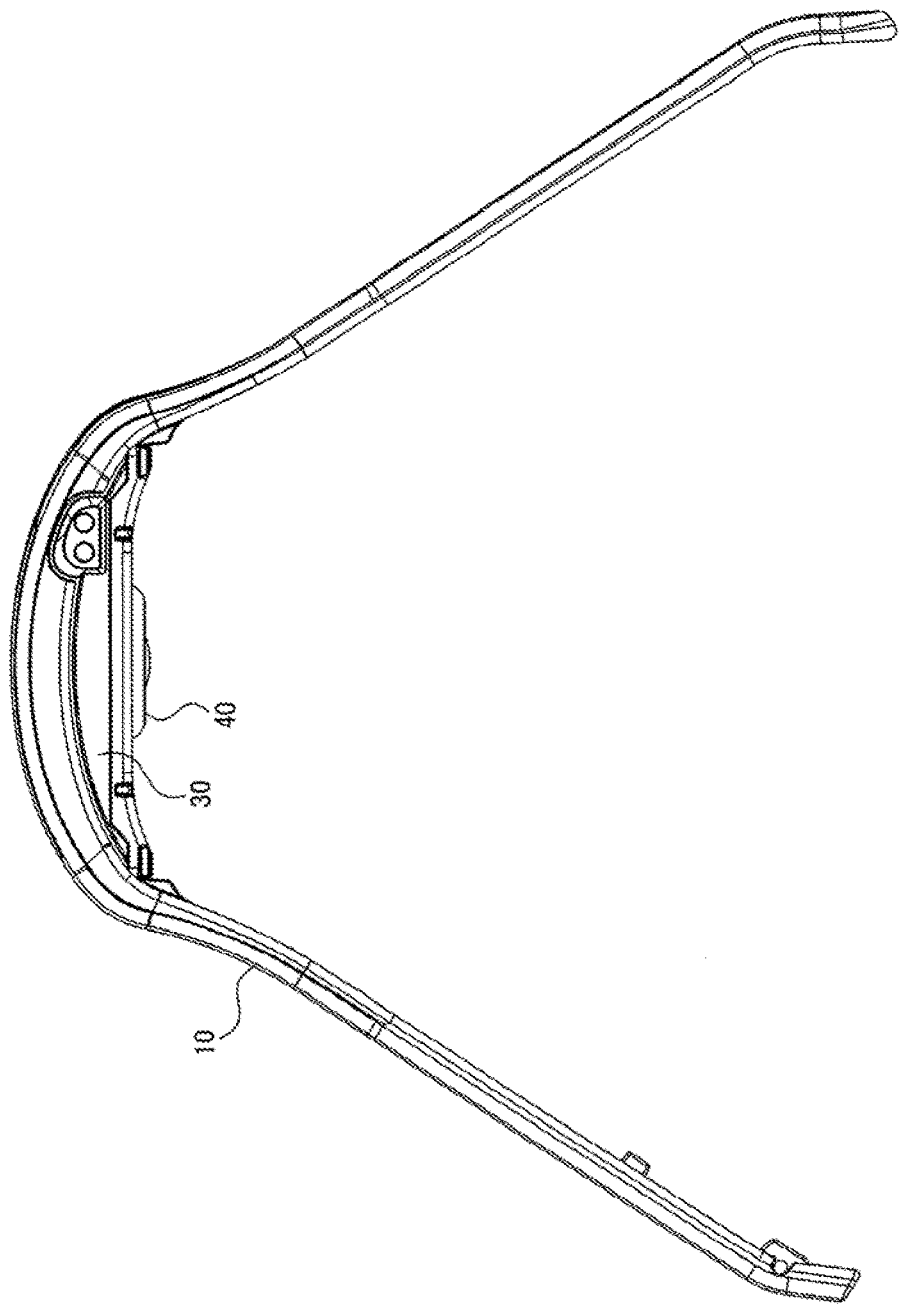
FIG. 5 is an appearance diagram of the biological information processing system (wearable apparatus) of this embodiment.

FIGS. 4A to 5 show an example of the appearance diagram of the wearable apparatus 200 when the biological information processing system 100 of this embodiment is implemented as the wearable apparatus 200. The wearable apparatus 200 of the embodiment has a bend part 10, a case part 30, and a sensor part 40. The case part 30 is attached to the band part 10. The sensor part 40 is provided in the case part 30.

The band part 10 is wound around the wrist of the user to mount the wearable apparatus 200. The band part 10 has band holes 12 and a buckle part 14. The buckle part 14 has a band insertion portion 15 and a protrusion 16. The user inserts one end of the band part 10 into the band insertion portion 15 of the buckle part 14 and inserts the protrusion 16 of the buckle part 14 into the band hole 12 of the band part 10, thereby mounting the wearable apparatus 200 on the wrist.

The case 30 corresponds to a main body of the wearable apparatus 200. Inside the case 30, various constituent components of the wearable apparatus 200, such as the sensor unit 40 and the processing unit 120, are provided. That is, the case 30 is a housing which stores these constituent components.

The case 30 is provided with a light emitting window portion 32. The light emitting window portion 32 is formed of a light transmissive member. Furthermore, the case 30 is provided with a light emitting part as an interface mounted on a flexible substrate, and light from the light emitting part is emitted to the outside of the case 30 through the light emitting window portion 32.

As shown in FIG. 6, the wearable apparatus 200 is mounted on the wrist of the user, and a measurement of pulse wave information (in a broad sense, biological information) is performed in a state where the wearable apparatus 200 is mounted.

The biological information processing system 100 according to this embodiment is not limited to the wearable apparatus 200 including the pulse wave sensor 101 and the like, and may be implemented as other electronic apparatuses. For example, the biological information processing system 100 of this embodiment may be a mobile terminal apparatus 300, such as a smartphone.

Figure 7:
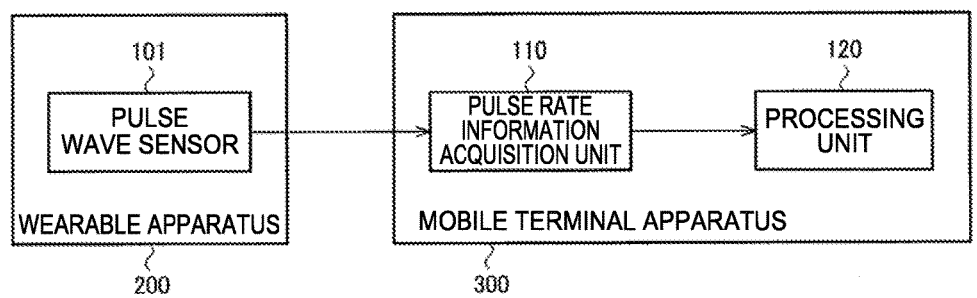
FIG. 7 shows another configuration example of the biological information processing system according to this embodiment.

In this case, as shown in FIG. 7, the mobile terminal apparatus 300 includes a pulse wave information acquisition unit 110 and a processing unit 120 corresponding to the biological information processing system 100, and the pulse wave information acquisition unit 110 acquires pulse wave information from a pulse wave sensor 101 mounted in the wearable apparatus 200 or the like. In this case, the wearable apparatus 200 and the mobile terminal apparatus 300 are connected by various networks, such as short distance radio communication. Though not shown in FIG. 7, the mobile terminal apparatus 300 may include a notification unit or a communication unit.

A specific example is shown in FIG. 6. In FIG. 6, the band type wearable apparatus 200 shown in FIG. 4A and the mobile terminal apparatus 300, such as a smartphone, are connected by short distance radio communication or the like, and index information relating to an arousal state calculated based on information from the pulse wave sensor 101 mounted in the wearable apparatus 200 is displayed on the display unit of the mobile terminal apparatus 300. In FIG. 6, the wearable apparatus 200 is provided with a notification unit (light emitting part). Therefore, the index information obtained by the mobile terminal apparatus 300 can be notified to the wearable apparatus 200. In this case, first, a procedure is performed, in which the wearable apparatus 200 transmits sensor information to the mobile terminal apparatus 300, and the mobile terminal apparatus 300 obtains index information using the sensor information and transmits the obtained index information to the wearable apparatus 200.

The electronic apparatus according to this embodiment is not limited to the wearable apparatus 200 or the mobile terminal apparatus 300, and various apparatuses, such as a personal computer (PC), can be used.

The biological information processing system 100 of this embodiment may be implemented as a system including a server system. A configuration example of the server system is the same as the mobile terminal apparatus 300 of FIG. 7. In this case, however, it is sufficiently considered that the server system is provided at a position physically far away from the user, and in this case, even if a processing result in the server system is notified by a notification unit of the server system, the user cannot recognize the processing result. Accordingly, in the server system, it is preferable to transmit a calculation result, such as index information, to an apparatus which is used by the user, such as the wearable apparatus 200 or the mobile terminal apparatus 300.

In general, the server system has high processing performance compared to the wearable apparatus 200 or the mobile terminal apparatus 300, and has little restriction on the storage area of the storage unit. Accordingly, it is possible to perform a process using pulse wave information at high speed compared to a case where the biological information processing system 100 is included in the wearable apparatus 200 or the like. Furthermore, if the storage area is large, it is possible to store log data of multiple users or to increase the amount of log data per person when acquires log data, such as pulse wave information. For this reason, it is possible to expect improvement of calculation accuracy of index information regarding the user by performing a universal process using multiple user data or storing pulse wave information of the user in terms of several years or several decades.

Various communication routes are considered between the wearable apparatus 200 and the server system. For example, if the wearable apparatus 200 is connectable directly to a network, the wearable apparatus 200 may perform communication directly with the server system through the network. Alternatively, the wearable apparatus 200 may first transmit sensor information to the mobile terminal apparatus 300 using short distance radio communication or the like, and communication may be performed between the wearable apparatus 200 and the server system through other apparatuses such that the mobile terminal apparatus 300 transfers the sensor information to the server system through a network.

4. Arousal Detection Method Based on Pulse Wave Information

Next, the details of an arousal detection method based on pulse wave information will be described. As described above, various factors for arousal are considered; however, as an example, a respiration disorder, such as sleep apnea syndrome, is exemplified. In the case of the respiration disorder, since a state of apnea or hypopnea is continued for about one minute and 30 seconds if long, it is considered that an oxygen deficient state is caused and arousal which is transient awakening occurs.

Figure 8:
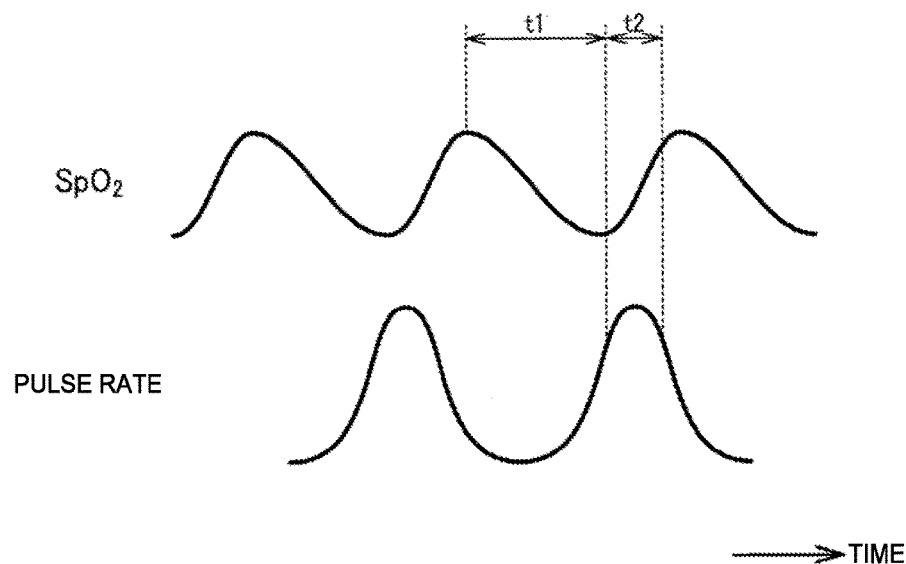
FIG. 8 is a diagram illustrating the relationship between arterial oxygen saturation and a temporal change in a pulse rate.

In this case, as shown in the upper portion of FIG. 8, because oxygenation in the lungs is not advanced while the apnea state is continued, the value of blood oxygen saturation (arterial oxygen saturation, $SpO_2$) is decreased with time. The horizontal axis of FIG. 8 represents a time, and the vertical axis represents the value of blood oxygen saturation or a pulse rate. When the apnea state is eliminated, the value of $SpO_2$ starts to be increased, and is returned to, for example, a normal value (a value close to 100%).

In FIG. 8, for example, it is considered that the apnea state is continued until $SpO_2$ starts to be increased after starting to be decreased at t1. In this case, it is considered that the arousal state is generated around the end of t1 in the oxygen deficient state.

In this embodiment, since the pulse wave information is used for a process, $SpO_2$ cannot be directly measured. However, in order to return $SpO_2$ to a normal state after $SpO_2$ is decreased, that is, to increase the value of $SpO_2$, a large amount of blood rich in oxygen needs to be supplied from the heart. That is, in a state where the apnea state is eliminated and respiration is possible, the pulse rate is increased compared to previous values. Then, if $SpO_2$ is returned to a normal range, the pulse rate is also returned to a normal value for a target user. This is shown in the lower portion of FIG. 8, and for example, the pulse rate has a peak, for example, at t2 which is the increasing section of $SpO_2$.

As will be understood from FIG. 8, even if it is difficult to directly detect an arousal state generated in the t1 section, if the peak of the pulse rate generated in the subsequent t2 section is detected corresponding to arousal, it is possible to detect the arousal state.

The arousal state is generated by a cyclic limb movement disorder, psychological stress, or the like; however, it is known that limb movement or psychological stress increases the pulse rate. That is, whatever the factor for arousal, it is considered that the pulse rate is significantly increased with respect to the normal value when arousal is generated. From this, in this embodiment, the arousal state is detected by detecting the increase.

However, it is known that the pulse rate is increased in the awake state (Stage Wake) compared to the sleep state. If the user takes exercise, such as sports, the pulse rate is obviously increased, and even if the body is moved lightly, the pulse rate is increased. Furthermore, even if the body is rested, the pulse rate is increased with psychological activity, such as thinking. That is, the increase in the pulse rate inevitably occurs in the awake state compared to the sleep state where various activities are restricted. Therefore, when transition is made from the sleep state to the awake state, the pulse rate is significantly increased.

For this reason, on a condition that the pulse rate is only increased, it is not possible to discriminate whether the increase corresponds to arousal or the awake state. Accordingly, in this embodiment, arousal is detected under the conditions that the pulse rate is returned to the normal value and the time required for changing a value is within a predetermined time, as well as the condition that the pulse rate is increased.

As described above, because arousal is transient awakening, even if the pulse rate is increased by arousal, the increase is not continuous and is supposed to be returned to the normal value. Furthermore, the time required for monitoring the change in the pulse rate once does not need to be long. For example, in the case of the respiration disorder described referring to FIG. 8, the change in the pulse rate requires a very long time to some extent and is supposed to fall within the t1+t2 section. Here, t1 is likely to be longer than t2, and the value thereof is a time of about one minute and 30 seconds as described above. From this, the predetermined time may be set to a value of about one minute and 30 seconds. Then, when the time required for changing the pulse rate exceeds the set predetermined time, it is possible to determine that the change occurs due to transition to the awake state, not arousal. Of course, as shown in FIG. 8, the change in the pulse rate may end in a shorter time. Therefore, if the change time of the pulse rate can be set qualitatively, a shorter time may be set as the predetermined time.

In other words, the pulse wave information is information representing the pulse rate, and the processing unit 120 sets the length of a second period tw based on a time corresponding to a change cycle of the pulse wave information which is information representing the pulse rate. When the change in the pulse rate or the like occurs within tw, it is determined that the change is due to the arousal state, not the awake state.

Information representing the pulse rate is not limited to the pulse rate, and may be similar information. For example, the pulse rate generally represents the number of beats in one minute; however, the pulse rate may represent the number of beats (specifically, the frequency of a pulse AC signal described below) in one second.

When tw set as above is used, if a change in a heart rate is due to the arousal state, it is expected that the change in the heart rate is performed within tw. For this reason, with the user of tw, it is possible to determine the arousal state based on the pulse rate with excellent accuracy.

Figure 9A:
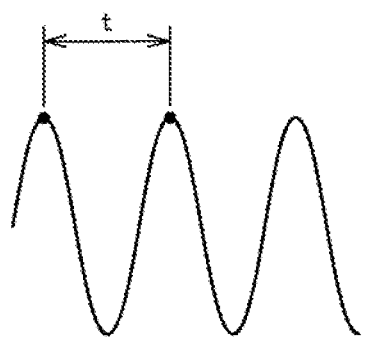
FIG. 9A is a diagram illustrating a pulse AC signal and a pulse period.

In the above description, although the pulse rate is used as the pulse wave information, other kinds of information, such as a pulse period (RR interval), may be used. The volume of blood flow of the user is repeated between a large volume state and a small volume state cyclically due to heartbeats. An AC component (pulse AC) in a pulse wave signal becomes information representing the variation. Therefore, it is possible to obtain the pulse rate (heart rate) or the pulse period using pulse AC. For example, it is assumed that a pulse AC signal is acquired as shown in FIG. 9A. The horizontal axis of FIG. 9A represents a time, and the vertical axis represents signal intensity. In this case, one cycle of the pulse AC signal having cyclicity corresponds to one beat of the heart. For this reason, the pulse rate (heart rate) is obtained from the frequency of the pulse AC signal, and the pulse period which is an interval for one beat of the heart becomes a time indicated by t of FIG. 9A. A normal pulse rate is the number of pulses per minute, and 60 times the frequency of pulse AC corresponds to a pulse rate which is generally used.

For this reason, the pulse wave information may be information representing a pulse period, and the processing unit 120 may set the length of the second period tw based on a time corresponding to a change cycle of the pulse wave information which is information representing the pulse period. In this case, information representing the pulse period includes information similar to the pulse period, such as information of an integer multiple of the pulse period.

That is, in this embodiment, the pulse wave information is the pulse rate or the pulse period in a narrow sense. However, the invention is not limited thereto, and various kinds of information can be used as the pulse wave information.

When the pulse period is used, the value of the pulse period is changed so as to be small due to arousal and then returned to the normal value. That is, in the above and following description, although a method using the pulse rate as the pulse wave information has been described or will be described, in this embodiment, the processing unit 120 obtains index information based on a change in pulse wave information in a broad sense.

The processing unit 120 may obtain index information based on a change in pulse wave information in a first period during which the user is in the sleep state. As described above, because arousal is transient awakening in brain waves, arousal cannot be generated when the user is already in the awake state (Wake). That is, when it is found to be the awake state, there is no need to perform arousal detection, and an efficient process is possible by targeting the pulse wave information of the sleep state to be detected.

Figure 10:
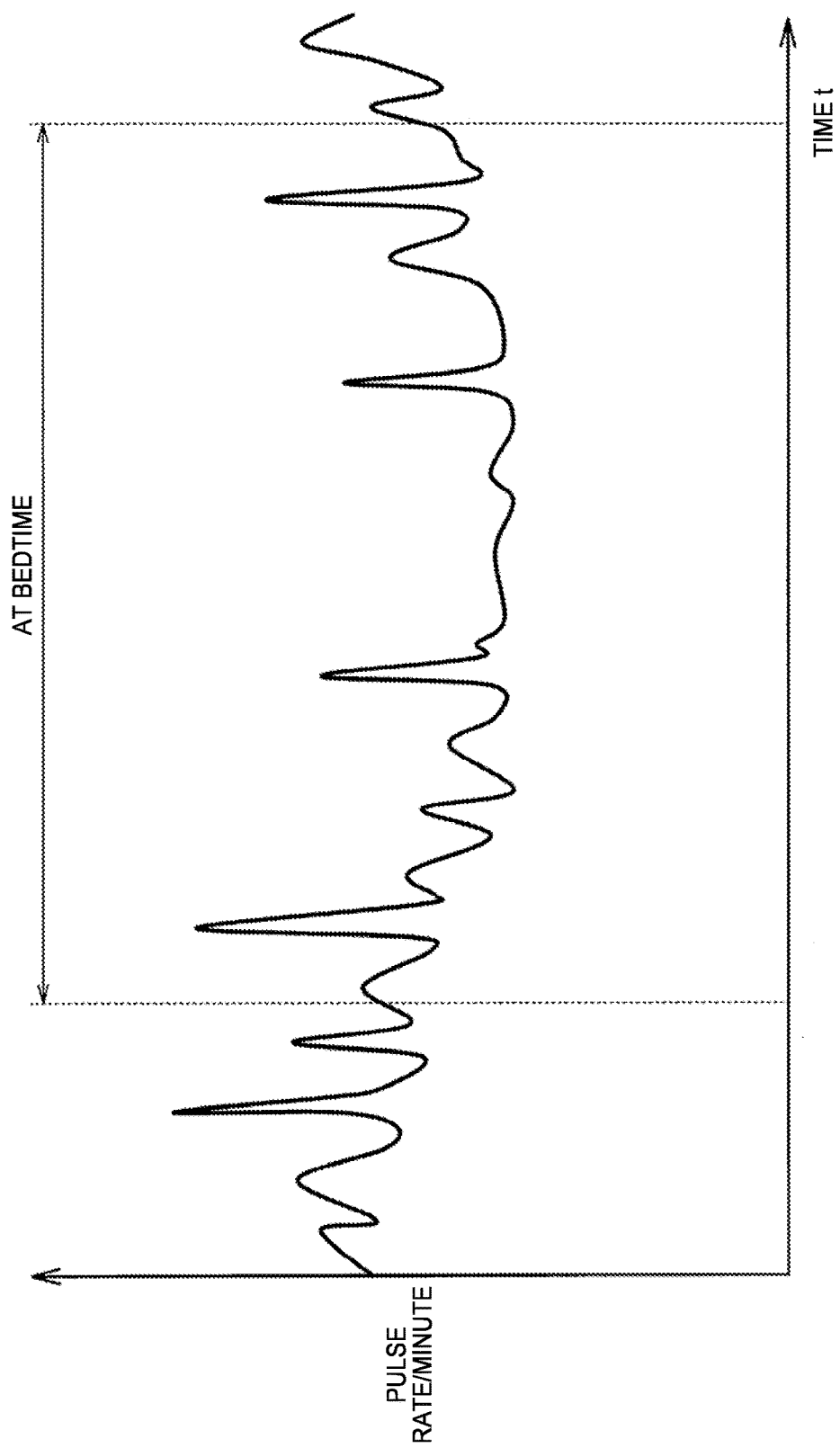
FIG. 10 is a diagram illustrating a temporal change in a pulse rate.

A specific process of this embodiment will be described referring to FIGS. 10 and 11. FIG. 10 is a graph showing a temporal change in a pulse rate of the user including a bedtime. The term "bedtime" refers to a state where the user gets into a bed and is in a rested state, and there is a possibility that the user is in a bed but is not in the sleep state. As described above, although the sleep state is determined thoroughly and arousal is then detected using the pulse wave information of the sleep state, arousal may be detected simply using pulse wave information at bedtime. Various modifications can be made, in which the body motion sensor 102 detects whether or not the user is during bedtime, or the user operates the operating unit 130 at the timing of getting into the bed.

As shown in FIG. 10, if a time-series pulse rate is acquired, a smoothing process of the pulse rate is performed. The smoothing process may be a process for obtaining a moving average or may be a process for obtaining a section average. When obtaining a section average, for example, averaging may be performed excluding the maximum and minimum of a pulse rate generated in a predetermined section.

Figure 11:
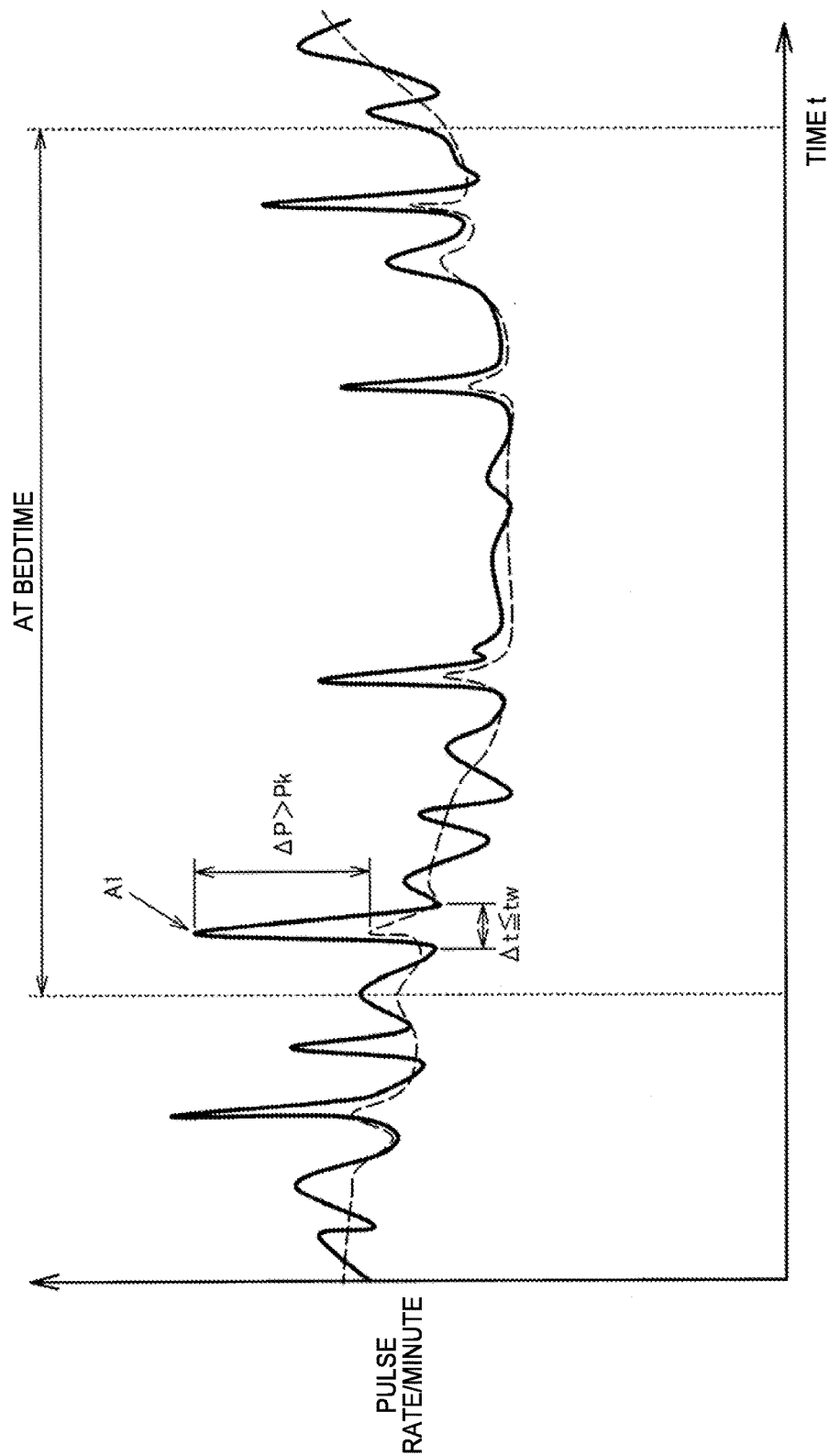
FIG. 11 is a diagram illustrating a pulse rate after a smoothing process, a change amount $\Delta P$, and a time $\Delta t$ corresponding to a peak width.

Information of the time-series pulse rate after the smoothing process is indicated by a broken line of FIG. 11. In FIG. 11, a smoothing process is performed outside a bedtime; however, as described above, a processing target may be limited to a time (or a time in the sleep state) in a bedtime state.

The processing unit 120 obtains index information based on a comparison process of the amount of change in pulse wave information in a given second period (a period of a length tw) and a given pulse wave change amount threshold value. Specifically, $\Delta P$ which is the amount of change (in the case of a pulse rate, the amount of increase) of the value of the pulse rate before the smoothing process with respect to the pulse rate after the smoothing process is obtained, and a comparison process of $\Delta P$ and a pulse wave change amount threshold value (in this case, a pulse rate change amount threshold value) Pk is performed. As described above, the condition of arousal is that the pulse rate is increased compared to the normal. Therefore, when $\Delta P$>Pk, there is a possibility that arousal is detected. When the pulse rate is used as the pulse wave information, Pk is, for example, a value of 4 to 5.

As described above, the change time $\Delta t$ of the pulse rate needs to be within a predetermined time interval tw. From this point, in the example of FIG. 11, a change in the pulse rate in a place indicated by A1 has the amount of change $\Delta P$ satisfying $\Delta P$>Pk, and $\Delta t$ satisfies $\Delta t \leq tw$. For this reason, single arousal is detected based on pulse wave information of a portion indicated by A1.

The processing unit 120 may obtain the number of times, at which the amount of change $\Delta P$ in the pulse wave information in the second period tw exceeds the pulse wave change amount threshold value Pk for a given unit time, as index information.

The given unit time is, for example, one hour. As described above, the normal range of the number of times of arousal is 10 to 20 times per hour. That is, there is a trend that if the sleep time is long, the number of times of arousal is large, and if the sleep time is short, the number of times of arousal is small. For this reason, while the number of times of arousal during one (a night) sleep can be used as an index, it is easy to use the count value of the number of times per unit time as an index value. If the given unit time is one hour, the user can estimate the quality of his/her sleep by determining whether the number of times of arousal per unit time as the index value falls below or exceeds 10 to 20.

In the above description, an example where a value of 4 to 5 is used as Pk when a pulse rate is used and a value of about one minute and 30 seconds is used as tw when a sleep disorder is considered has been described. Pk or tw does not need to be a fixed value, and can be flexibly set from various viewpoints. For example, the processing unit 120 may set at least one value of the second period tw and the pulse wave change amount threshold value Pk based on personal information of the user.

For example, age may be used as personal information. It is considered that responsiveness of a pulse rate with a change in an activity state is changed according to age. In general, the responsiveness becomes higher when the age is lower, and the responsiveness becomes lower when the age is higher. That is, in the case of a younger user, even if Pk is set to be high, it is possible to establish $\Delta P$>Pk when arousal is generated, and in regard to a change in pulse wave information which may be caused due to a factor other than arousal, or a measurement error, it is possible to establish $\Delta P$ to be equal or less than Pk. As a result, it is possible to perform determination with excellent accuracy. Meanwhile, an older user has low responsiveness. Therefore, in the setting of Pk similar to young people, even if arousal is generated, a situation in which arousal cannot be detected may occur. In consideration of the above, Pk may be set to be large when the age is lower, and Pk may be set to be small when the age is higher.

A medical history, an interesting arousal factor, or the like may be considered as personal information. As described above, arousal has various factors. In a respiration disorder, an apnea state is continued long, and as a result, a single change in $SpO_2$ may occur over a comparatively long time (a change cycle may be long). As described referring to FIG. 8, the pulse rate has relevance to $SpO_2$. From this, tw may be a long period to a certain degree (for example, a degree corresponding to one cycle of the change in $SpO_2$). In contrast, in the case of a cyclic limb movement disorder, arousal is generated at the timing when limb movement occurs, and if the movement ends, the pulse rate is supposed to be returned to the normal in a comparatively short time. That is, it is also possible to change tw according to what factor is focused as a factor for arousal.

Pk may be set using the history of pulse wave information of the user. For example, Pk may be set in consideration of a standard deviation $\sigma$ obtained from variation of a pulse rate in a predetermined section and a preceding or succeeding section and an instance frequency according to the number of pieces of data in the predetermined section. The average and variation of the pulse rate in the section and the preceding or succeeding section have no significant difference. For example, if a section is one minute, and data in the section is calculated for every second, the number of pieces of data becomes 60. That is, if the preceding or succeeding section is included, $\sigma$ is obtained for the number of pieces of data, 180. Pk may be a value capable of determining to be significantly different from the pulse rate during the normal. Therefore, when $\sigma$ is obtained, a value (for example, Pk=$2.33 \times \sigma$) of an integer multiple of $\sigma$ can be used.

Figures 12, 13:
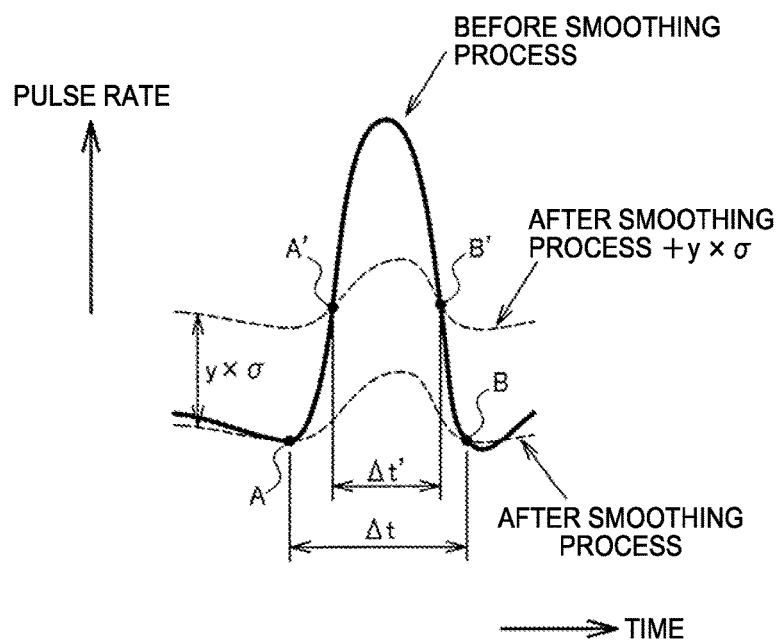
FIG. 12 shows a setting example of a pulse wave change amount threshold value Pk according to age.
FIG. 13 is an explanatory view of a method of obtaining a peak width of a peak of a pulse rate.

A table shown in FIG. 12 is an example where the setting of Pk according to age and the setting of Pk using $\sigma$ are combined. As will be understood from FIG. 12, Pk is set to a value of an integer multiple of $\sigma$; however, the coefficient is large, 3, for younger people (20 to 40 years old), the coefficient is decreased to 2.58 for 40 to 50 years old people, and the coefficient is set to be low, 1.96, for older people (more than 50 years old). In FIG. 12, while the age is divided into five stages, various modifications can be made for the setting of Pk, in which the number of stage divisions is changed, a monotone decreasing function f(x) on an age x is defined, and f(x) is set as a coefficient when setting Pk.

Various modifications can be made to the method of obtaining the change time $\Delta t$ of the pulse rate. In a case of FIG. 13, it is considered that intersections A and B of the value of the pulse rate before the smoothing process and the value of the pulse rate after the smoothing process are obtained, and the time between A and B is set as $\Delta t$. However, the positions of these intersections on the horizontal axis may be changed largely due to a certain error. For example, even if the shape of the peak itself is similar, a plain portion is widened or narrowed depending on the state of the intersection. Here, the peak width of a peak of pulse wave information is inherently used in the comparison process with tw. Accordingly, in this embodiment, a value changed by $y \times \sigma$ (y is a given constant) with respect to the value of the pulse wave information after the smoothing process may be considered, and Δt may be obtained based on the value. Specifically, intersections A' and B' shown in FIG. 13 may be obtained, and the time between A' and B' may be set as Δt. Alternatively, a section in which a change in the pulse rate before the smoothing process with the pulse rate after the smoothing process exceeds y×σ in succession may be measured and set as Δt. Then, it is possible to obtain Δt appropriately reflecting the peak width.

Figure 14:
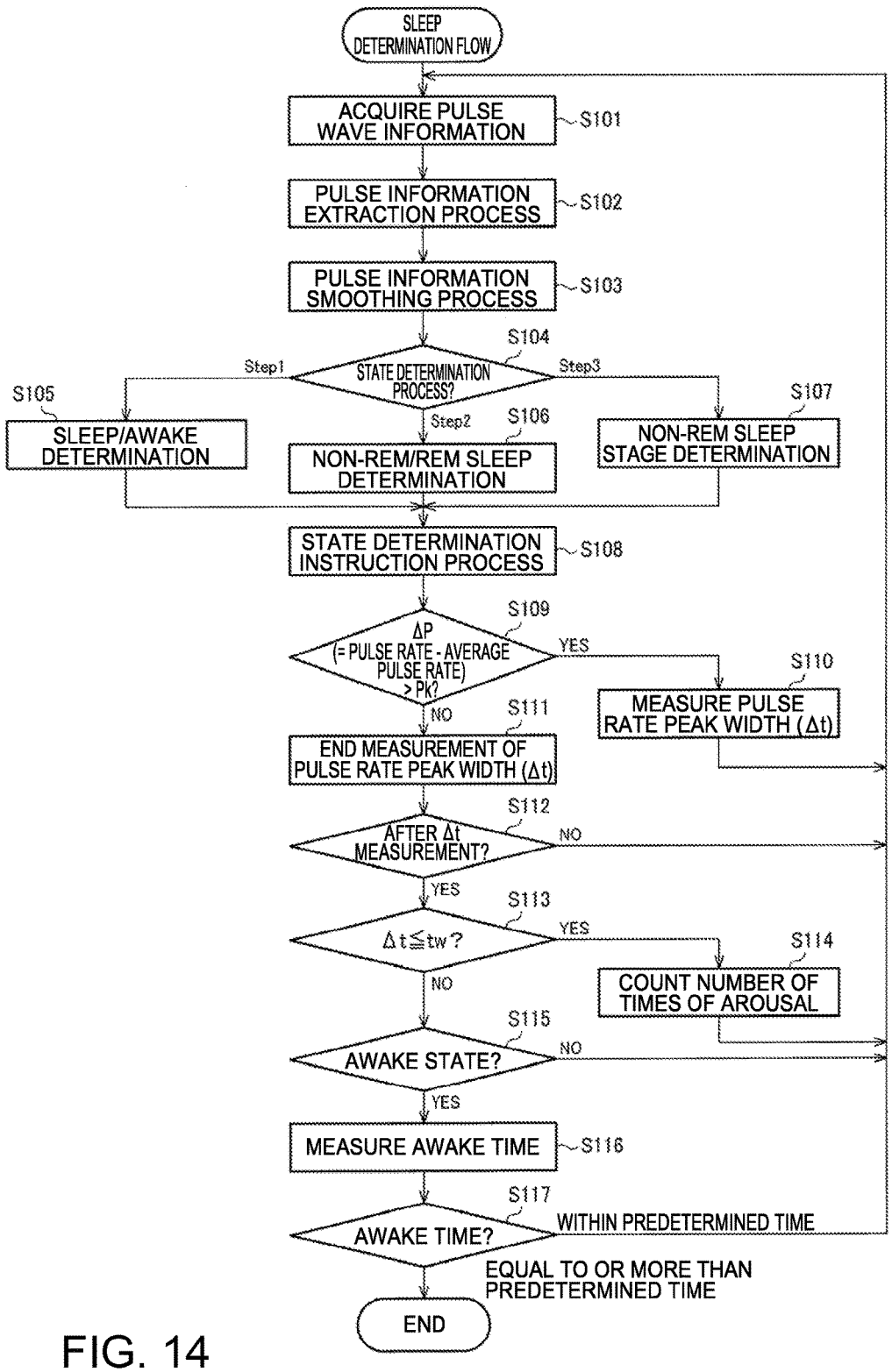
FIG. 14 is a flowchart illustrating a process of this embodiment.

FIG. 14 is a flowchart illustrating the process of this embodiment described above. If the process is started, first, the pulse wave information acquisition unit 110 acquires pulse wave information (S101), and the processing unit 120 performs a process on the pulse wave information. Specifically, a process for extracting pulse information (for example, a pulse rate or a pulse period) based on the pulse wave information is performed (S102), and a process for smoothing the obtained pulse information is performed (S103).

Next, a determination process which is performed as a process for determining the state is selected (S104). As specific determination, determination of a sleep state or an awake state (S015), in the case of the sleep state, determination of a REM sleep state or a non-REM sleep state (S106), and in the case of the non-REM sleep state, determination of any stage (any of Stage 1 to Stage 4) of the non-REM sleep state (S107) are considered. If the determination content is selected, the execution of the selected determination is instructed (S108).

In a process for obtaining index information of an arousal state in this embodiment, the process of S106 or S107 is not essential. However, considering that arousal is an index value relating to sleep, it can be said that it is useful to perform S106 or S107 of obtaining detailed state of sleep in combination. The determination of S105 is not essential; however, a modification can be used, in which, first, the sleep state is determined, and then, as described above, the process after S109 is performed for the pulse wave signal of the sleep state.

Next, ΔP which is the amount of change in the pulse rate before the smoothing process with respect to the pulse rate after the smoothing process is obtained, and a comparison process with a given pulse wave information threshold value (pulse rate threshold value) Pk is performed (S109). When ΔP>Pk, there is a possibility that the amount of change ΔP is a change in the pulse rate due to arousal. Therefore, the measurement of the peak width (Δt) is performed (S110). After S110, the procedure returns to S101, and the process is continued.

If ΔP≤Pk, the measurement process of the peak width Δt of the pulse rate ends (S111). Then, it is determined whether or not Δt is measured (S112), and when the determination is No, the count of arousal or the like is not required, and thus, the procedure returns to S101.

When Δt is measured, a comparison process of Δt as the measurement result and a given time interval tw is performed (S113). When Δt≤tw, the above-described condition is satisfied. Therefore, it is determined that a change in the pulse rate corresponding to ΔP is caused by arousal, and the count process of arousal (in a narrow sense, a process for increasing the number of times of arousal) is performed (S114).

When Δt>tw, it is determined that a change in the pulse rate corresponding to ΔP is not caused by arousal. Therefore, the count process of arousal is not performed. When Δt>tw, since an increase in the pulse rate over a comparatively long time is found, there is a possibility of transition to the awake state (Wake). Therefore, it is determined whether or not the user is the awake state (S115).

When the determination is No in S115, the sleep state is continued, and arousal is likely to be generated. Therefore, the procedure returns to S101 and the process is continued. When the determination is Yes in S115, the time when the user is in the awake state is measured (S116), and it is determined whether or not the time is within a predetermined time (S117).

When it is determined in S117 that the time is within the predetermined time, the awake state is transient and is likely to be instantly returned to the sleep state. Therefore, the procedure returns to S101 and the process is continued. Transient awakening represents awakening, which the user can recognize, such as a state where the user awoke to go to the bathroom at night, but is not arousal.

When it is determined in S117 that the time is equal to or longer than the predetermined time, the awake state is persistent (for example, a state where a user having a general life rhythm wakes up morning), and it can be determined that there is no transition to the sleep state. In this case, since it is not necessary to perform a detection process of arousal, the process ends.

In conclusion, the processing unit 120 of this embodiment performs the smoothing process on the pulse wave information in a period (first period) during which it is determined that the user is in the sleep state (corresponding to S103), obtains the change in the pulse wave information before the smoothing process with respect to the value of the pulse wave information after the smoothing process as the amount of change ΔP of the pulse wave information (corresponding to S109), when the amount of change exceeds the given pulse wave change amount threshold value Pk (in S109, Yes), obtains the time representing the width Δt of the peak of the pulse wave information corresponding to the amount of change (corresponding to S110), when the obtained time Δt is within the given time interval (second period) tw (in S113, Yes), determines that the arousal state is generated, and obtains the index information (as an example, the count processing result in S114) based on the determination result.

5. Example of Display Screen

The processing unit 120 obtains somnolence index information as the index information relating to the arousal state. The somnolence index information is information which may become an index relating to a somnolent state. Somnolence represents the degree of a consciousness disorder, and refers to a state where awakening is possible by external stimulation, and consciousness instantly fades. The somnolent state may represent a state of somnolence itself, and in a broad sense, may indicate a state where sleepiness is strong compared to the normal (a state where a healthy user does not feed sleepy), or a state where consciousness fades. That is, the somnolence index information is simply information representing the degree of intensity of sleepiness of the user.

Various specific examples of the somnolence index information in this embodiment are considered. Here, for example, a case where the somnolence index information is displayed will be described. A display unit on which information is to be displayed may be a display unit included in the biological information processing system 100, like the display unit 160 shown in FIG. 3, or may be a display unit provided an external apparatus which receives the somnolence index information through the communication unit 180.

For example, when the biological information processing system 100 is constituted by the single wearable apparatus 200, the somnolence index information may be displayed on the display unit of the wearable apparatus 200. Furthermore, when the biological information processing system 100 includes the wearable apparatus 200 and the mobile terminal apparatus 300, as shown in FIG. 6, the somnolence index information may be displayed on the display unit of the mobile terminal apparatus 300. In addition, in the configuration of FIG. 6, if the biological information processing system 100 is constituted by the wearable apparatus 200 and does not include the mobile terminal apparatus 300, the somnolence index information is displayed in an external apparatus.

As described above, it is considered that, when the number of times of detection of arousal per unit time is larger, sleep is disturbed and the quality of sleep of the user is bad. Therefore, as shown in FIG. 6, the number of times of detection of arousal may be used as somnolence index information as it is. In FIG. 6, the number of times of detection of arousal for the entire sleep time and the average number of times of detection per unit time are displayed in combination.

The term "arousal" is generally used in a research field; however, a user who is not an expert may be difficult to understand the term "arousal". For this reason, as shown in FIG. 15A, arousal may be changed to an easy-to-understand expression, such as "unconscious wake-up".

Figures 15A, 15B, 15C:
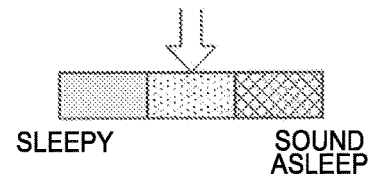
FIGS. 15A to 15C show a display screen example where somnolence index information is displayed.

Alternatively, as shown in FIG. 15B, the degree of sleepiness in the awake state may be obtained based on the number of times, and the result may be displayed. In other words, the biological information processing system 100 presents sleepiness prediction indicating a possibility of the user feeling sleepy based on information relating to the arousal state.

Information regarding whether there is a possibility that a target user strongly feels sleepy or not is displayed by the term "diurnal sleepiness prediction". Specifically, if there is a possibility that sleepiness is strong, this is defined as "sleepy". Conversely, when it is estimated that the quality of sleep is good and sleepiness is a little, this is defined as "a little". The middle is defined as "somewhat sleepy". In this case, determination may be performed using the number of times of detection of arousal per unit time and a given threshold value, and a stage to be selected may be determined from the determination result. For example, threshold values Th1 and Th2 are set, a case where the number of times of detection Id of arousal per unit time is Id≥Th1 is defined as "sleepy", a case where Th2≤Id<Th1 is defined as "somewhat sleepy", and a case where Id<Th2 is defined as "a little sleepy". Here, Th1 is, for example, 30 (times/hour), and Th2 is 20 (times/hour).

Alternatively, as shown in FIG. 15C, visual expression may be made using a figure or the like. In FIG. 15C, a crossbar graph is colored into three stages, the left is "sleepy", and the right is "sound asleep". That is, the horizontal axis represents that the quality of sleep is worse toward the left, and the quality of sleep is better toward the right. In the graph, an arrow is displayed at a position representing the quality of sleep corresponding to the user. In the example of FIG. 15C, the user represents that the user gets sleep of intermediate quality. The display position of the arrow in FIG. 15C may be determined by the number of times of arousal per unit time similarly to the example of FIG. 15B. Specifically, threshold value determination in three stages may be performed similarly to FIG. 15B, and the position may be adjusted more finely according to the number of times of detection of arousal. For example, when the left end of the horizontal axis is 0 (times/hour) and the right end is Imax (times/hour), and when the number of times of detection of arousal of the user is Id, a display method which displays an arrow at a position according to the ratio of Id/Imax from the left end in the entire graph (however, so as not to go toward the right from the right end) is considered.

In the above description, although the somnolence index information is displayed on the display unit, the invention is not limited thereto. For example, as shown in FIG. 4A and the like, when the biological information processing system 100 has a light emitting part as a presentation unit, the somnolence index information may be presented by a light emission pattern of the light emitting part. The light emission pattern is a pattern which is determined by a light emission color, a light emission time, a blinking interval, or the like. Alternatively, a vibration part may be used as a presentation unit, and the somnolence index information may be presented by a vibration pattern. The vibration pattern is a pattern which is determined by vibration intensity, a vibration time, a vibration interval when vibration and stop are repeated, or the like.

6. Determination Method of Sleep State and Awake State Based on Pulse Wave Information Though not an essential process in this embodiment, the biological information processing system 100 may determine the sleep state based on the pulse wave information. Specifically, it may be determined whether the user is in the sleep state or the awake state based on the pulse wave information, and when the user is in the sleep state, the depth of sleep may be determined (in a narrow sense, it may be determined whether the user is in the REM sleep state or the non-REM sleep state). This method will be described.

As described above, if the pulse AC signal shown in FIG. 9A is acquired, the pulse rate (heart rate) is obtained from the frequency of the pulse AC signal, and the pulse period which is an interval corresponding to one heartbeat becomes the time indicated by t of FIG. 9A.

The processing unit 120 of this embodiment may determine an autonomic nerve activity state based on the pulse wave information and may perform determination of the sleep state and the awake state based on the autonomic nerve activity state.

The autonomic nerve includes a sympathetic nerve and a parasympathetic nerve, and the activity state thereof has a diurnal or seasonal variation. In general, the sympathetic nerve is given priority during diurnal activity, and the parasympathetic nerve is given priority during nocturnal activity. In terms of the season, the sympathetic nerve is given priority from autumn to winter, and the parasympathetic nerve is given priority from spring to summer. It seems that the user can sleep well in spring because the parasympathetic nerve is given priority. In this way, for transition from the awake state to the sleep state, it is necessary that the parasympathetic nerve is changed with priority over the sympathetic nerve. In the determination of the sleep state, it is possible to observe the autonomic nerve activity state based on the pulse period obtained from the pulse wave information.

In order to determine the autonomic nerve activity state from the pulse wave information, first, the pulse period indicated by t of FIG. 9A is measured in a certain period, thereby acquiring time-series data of the pulse period. The pulse period is not always constant and has a variation (fluctuation). It is known that the variation is caused by the activity of the sympathetic nerve and the activity of the parasympathetic nerve, and that the degree of variation by the activity of the sympathetic nerve is different from the degree of variation by the activity of the parasympathetic nerve.

Figure 9B:
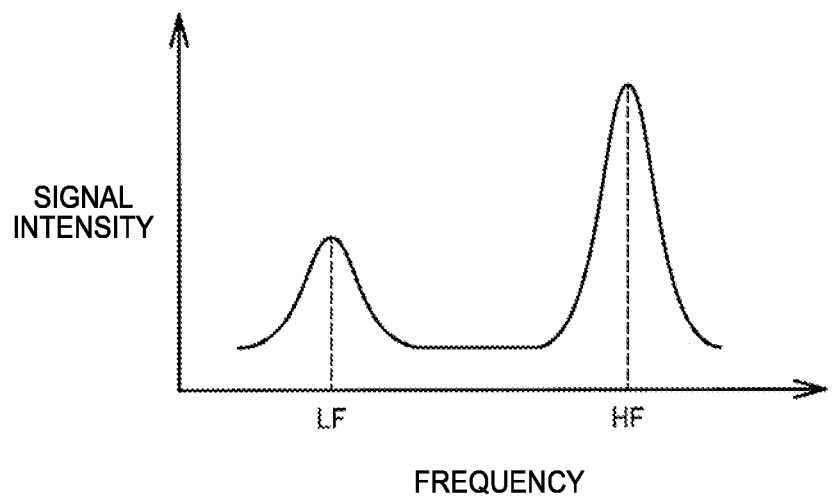
FIG. 9B is a diagram illustrating a process for obtaining LF and HF from pulse wave information.

Accordingly, time-series data of the pulse period is frequency-converted. An example of data after frequency conversion is shown in FIG. 9B. As will be understood from FIG. 9B, a peak LF of a comparatively low frequency and a peak HF of a comparatively high frequency are acquired from data after frequency conversion.

LF represents a slow change in the pulse period, and primarily reflects the activity of the sympathetic nerve. In contrast, HF represents a quick change in the pulse period, and primarily reflects the activity of the parasympathetic nerve. Strictly, LF may reflect both the sympathetic nerve and the parasympathetic nerve; however, in the following description, a case where LF primarily reflects the activity of the sympathetic nerve will be described for simplification of description.

Considering such characteristics, the ratio of LF and HF (for example, the ratio of signal intensity at the respective peaks) is obtained, whereby it is possible to determine whether the sympathetic nerve or the parasympathetic nerve is given priority in the measurement period of the pulse wave information.

Various methods of determining the sleep state from LF and HF are considered; however, for example, the value of LF/HF may be used. LF/HF is large when the sympathetic nerve is given priority, and becomes a small value when the parasympathetic nerve is given priority. Therefore, a first threshold value Th1 may be set, if LF/HF>Th1, it may be determined to be the awake state because the sympathetic nerve is given priority, and if LF/HF≤Th1, it may be determined to be the sleep state because the parasympathetic nerve is given priority. In regard to the sleep state, a second threshold value Th2 (<Th1) may be set, if Th1≥LF/HF>Th2, it may be determined that sleep is light (REM sleep state) because the sympathetic nerve is comparatively given priority in the sleep state, and if LF/HF≤Th2, it may be determined that sleep is deep (non-REM sleep state) because the parasympathetic nerve is given priority. If the determination (S107 in the flowchart of FIG. 14) of a stage in the non-REM sleep state is performed, an additional threshold value may be provided in the non-REM sleep state, and the determination may be performed.

Not only the determination using simple values described above, but also a process may be performed using history information, such as previous pulse wave data of a target user. For example, if the history is referred to, it is possible to estimate the characteristic of cyclicity (for example, the time required for one cycle of the REM sleep state and the non-REM sleep state) in the sleep state of the target user. It is understood that, in one cycle, non-REM sleep continuously appears to some extent, and thereafter, REM sleep continuously appears to some extent. Therefore, when the determination using LF and HF is adverse to the assumption, it is possible to estimate that there is a high possibility of erroneous determination. In addition, a situation in which erroneous determination is likely to occur for each user, or the like can be learned. Therefore, it is possible to expect improvement of determination accuracy using the learning result. Besides, various modifications can be made to the determination of the sleep state using LF and HF.

Although this embodiment has been described above in detail, those skilled in the art will readily appreciate that many modifications are possible in the embodiments without materially departing from the novel teachings and advantages of the invention. Accordingly, all such modifications are intended to be included within the scope of the invention. Any term cited with a different term having a broader meaning or the same meaning at least once in the specification and the drawings can be replaced by the different term in any place in the specification and the drawings. The configuration and the operation of the biological information processing system are not limited to those described in connection with this embodiment. Various modifications and variations may be made of those described in connection with this embodiment.

What is claimed is:

1. A biological information processing system comprising:
   a pulse wave sensor;
   a pulse wave information acquisition unit which acquires pulse wave information of a user from the pulse wave sensor; and
   a processing unit which determines the sleep state of the user based on the pulse wave information, and
   a presentation unit which presents the index information to the user;
   wherein the processing unit obtains index information relating to a brain wave state during sleep based on the pulse wave information, and
   wherein the processing unit:
      performs a smoothing process of the pulse wave information in a first period during which it is determined that the user is in the sleep state;
      obtains an amount of change of a peak of the pulse wave information before the smoothing process with respect to the value of the peak of the pulse wave information after the smoothing process;
      when the obtained amount of change of the peak exceeds a pulse wave change amount threshold value, obtains a time representing the width of the peak of the pulse wave information; and
      when the obtained time is within a given second period, determines that the arousal state is generated and obtains the index information based on the determination result.

2. The biological information processing system according to claim 1,
   wherein the brain wave state is an arousal state.

3. The biological information processing system according to claim 1,
   wherein the processing unit obtains the index information based on a change in the pulse wave information in a first period during which it is determined that the user is in the sleep state.

4. The biological information processing system according to claim 3,
   wherein the processing unit obtains the index information based on a comparison process of the amount of change in the pulse wave information in a given second period and a pulse wave change amount threshold value.

5. The biological information processing system according to claim 4,
   wherein the processing unit obtains, as index information, the number of times at which the amount of change in the pulse wave information in the second period exceeds the pulse wave change amount threshold value for a given unit time.

6. The biological information processing system according to claim 4, wherein the processing unit sets at least one value of the length of the second period and the pulse wave change amount threshold value based on personal information of the user.

7. The biological information processing system according to claim 4,
wherein the pulse wave information is information representing a pulse rate or a pulse period, and
the processing unit sets the length of the second period based on a time corresponding to a change cycle of the pulse wave information.

8. The biological information processing system according to claim 2,
wherein the processing unit obtains somnolence index information as the index information relating to the arousal state.

9. The biological information processing system according to claim 2,
wherein the processing unit detects a state representing awakening without user consciousness as the arousal state based on the pulse wave information.

10. The biological information processing system according to claim 1,
wherein the pulse wave information is a pulse rate or a pulse period.

11. The biological information processing system according to claim 1,
wherein the presentation unit presents that the user is in the arousal state.

* * * * *